United States Patent
Liu

(10) Patent No.: US 9,663,439 B2
(45) Date of Patent: May 30, 2017

(54) AILDENAFIL CITRATE CRYSTAL FORM O, PREPARATION METHOD AND USE THEREOF

(76) Inventor: Guikun Liu, Guangdong (CN)

( * ) Notice: Subject to any disclaimer, the term of this patent is extended or adjusted under 35 U.S.C. 154(b) by 0 days.

(21) Appl. No.: 13/583,511

(22) PCT Filed: Mar. 11, 2011

(86) PCT No.: PCT/CN2011/071725
§ 371 (c)(1),
(2), (4) Date: Sep. 7, 2012

(87) PCT Pub. No.: WO2011/140858
PCT Pub. Date: Nov. 17, 2011

(65) Prior Publication Data
US 2013/0165448 A1    Jun. 27, 2013

(30) Foreign Application Priority Data

May 10, 2010 (CN) .......................... 2010 1 0172926

(51) Int. Cl.
| *C07D 487/04* | (2006.01) |
| *A61K 31/519* | (2006.01) |
| *A61P 15/10* | (2006.01) |
| *C07C 51/43* | (2006.01) |
| *C07C 59/265* | (2006.01) |
| *A61K 9/16* | (2006.01) |
| *A61K 9/20* | (2006.01) |

(52) U.S. Cl.
CPC ............ *C07C 51/43* (2013.01); *A61K 9/1623* (2013.01); *A61K 9/1635* (2013.01); *A61K 9/1641* (2013.01); *A61K 9/1652* (2013.01); *A61K 9/2018* (2013.01); *A61K 9/2027* (2013.01); *A61K 9/2031* (2013.01); *A61K 9/2054* (2013.01); *C07C 59/265* (2013.01); *C07D 487/04* (2013.01)

(58) Field of Classification Search
CPC ........................... C07D 487/04; A61K 31/519
USPC ...................................... 544/262; 514/252.16
See application file for complete search history.

(56) References Cited

FOREIGN PATENT DOCUMENTS

CN           101671339        *    3/2010

* cited by examiner

*Primary Examiner* — Susanna Moore
(74) *Attorney, Agent, or Firm* — Gokalp Bayramoglu

(57) ABSTRACT

The invention provides a 1-[3-(6,7-dihydro-1-methyl-7-oxo-3-propyl-1H-pyrazolo[4,3-d] pyridine-5-group)-4-ethoxy-benzenesulfonyl]-cis-3,5-dimethylpiperazine citrate or an Aildenafil citrate crystal form O and a preparation method thereof. And the invention also provides pharmaceutical compositions containing the Aildenafil citrate crystal form O and the use thereof in preparing drugs for treating Male Erectile Dysfunction (ED). The above crystal form O can be prepared through the steps of: dissolving a raw material, namely, the Aildenafil citrate in a mixture of distilled water and tetrahydrofuran, stirring, heating, filtering, stirring a filtrate, cooling, insulating heat, crystallizing, filtering and the like. The crystal form O can be adopted to prepare drugs with pharmaceutically acceptable excipients, so as to treat the male sexual dysfunction diseases.

7 Claims, 4 Drawing Sheets

AILDENAFIL CITRATE CRYSTAL FORM O, PREPARATION METHOD AND USE THEREOF

FIELD OF THE INVENTION

The invention relates to a crystal form O of 1-[3-(6,7-dihydro-1-methyl-7-oxo-3-propyl-1H-pyrazolo[4,3-d] pyridine-5-group)-4-ethoxy-benzenesulfonyl]-cis-3,5-dimethyl-piperazine citrate (Aildenafil citrate), and a preparation method, pharmaceutical compositions containing the crystal form O provided by the invention, and the use of the crystal form O in preparing drugs for treating Male Erectile Dysfunction (ED). This application is based on the Chinese invention patent application, of which the application date is May 10, 2010, and the application number is 201010172926.0; the contents of the above patent application are introduced into this text as a reference.

BACKGROUND OF THE INVENTION

ED is a common disease, mainly defined as that, the penis cannot erect, the penis cannot ejaculate, or both; according to statistics, the incidence of ED suffered by men over the age of 40 takes 1.9%, and the incidence of ED suffered by men over the age of 65 reaches 65%. There are approximately 125 million men suffering ED in different degrees in the world; and it estimates that 322 million men may suffer ED in 2025 (Moreland R B, et al, J Pharmacol Expther, 2001, 296 (2): 225-234). Thus, it has very important clinical values and social benefits for researching and developing new safe and effective drugs or new drug delivery systems to treat ED. And for this reason, some new drugs with novel structures and unique action mechanisms are promoted to the market or are being implemented with clinical researches and preclinical studies.

The Aildenafil citrate, of which the chemical name is 1-[3-(6,7-dihydro-1-methyl-7-oxo-3-propyl-1H-pyrazolo[4,3-d] pyridine-5-group)-4-ethoxy-benzenesulfonyl]-cis-3,5-dimethylpiperazine citrate, the molecular formula is $C_{23}H_{32}N_6O_4S \cdot C_6H_8O_7$, the molecular weight is 680.73, and the chemical structure is:

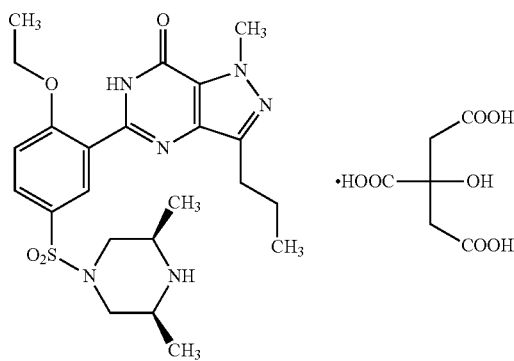

is a new drug which is implemented with the clinical research and is effective for treating ED. The Chinese patent (of which the application number is 02100198.7) discloses the Aildenafil citrate and the preparation method thereof and the like, but does not relate to the Aildenafil citrate crystal form and the preparation method thereof.

During the process of researching and preparing the Aildenafil citrate, the invention finds that the Aildenafil citrate has multiple crystal forms; the crystal form O provided by the invention has high biological activity, high purity, good stability and excellent industrial production, is suitable for the technical process of the preparations, and is suitable for long-term storage.

SUMMARY OF THE INVENTION

The purpose of the invention is to research an Aildenafil citrate crystal form O and a preparation method of the Aildenafil citrate crystal form O; and another purpose of the invention is to research pharmaceutical compositions containing the Aildenafil citrate crystal form O and the use of the Aildenafil citrate crystal form O in preparing drugs for treating ED.

The content of the invention is described in details with reference to the purposes of the invention.

The invention provides an Aildenafil citrate crystal form O, wherein the characteristic absorption peaks (2θ) of the Powder X-Ray Diffraction (PXRD), the D values and the relative intensities of the crystal form are as follows, and the error of the 2θ diffraction angles is +/−0.2.

| Diffraction angle (2θ) | D value | Relative intensity (%) |
|---|---|---|
| 7.600 | 11.6227 | 100 |
| 10.160 | 8.6992 | 42 |
| 13.780 | 6.4210 | 18 |
| 14.220 | 6.2233 | 32 |
| 14.980 | 5.9092 | 48 |
| 16.900 | 5.2419 | 19 |
| 18.580 | 4.7716 | 20 |
| 18.960 | 4.6768 | 32 |
| 19.300 | 4.5952 | 24 |
| 20.980 | 4.2308 | 15 |
| 22.700 | 3.9140 | 27 |
| 23.740 | 3.7448 | 27 |
| 24.700 | 3.6014 | 16 |
| 25.520 | 3.4875 | 16 |

The PXRD is normally used for determining the structures of the multiple crystal forms, researching the thermodynamic stability and implementing other qualitative and quantitative researches, so it is one of the most commonly-used methods for researching multiple crystal forms of the drugs.

In the invention, the precision of a light source used for measuring the 2θ value is +/−0.2°, indicating that the above value allows to be taken with a certain reasonable error range, and the error range is +/−0.2°; the strongest characteristic absorption peak (2θ) of the crystal form O is 7.600.

The infrared spectrogram of the crystal form O has the characteristic absorption peaks which can distinguish the crystal form O with other crystal forms in 3423+/−5 $cm^{-1}$, 3310+/−5 $cm^{-1}$, 3193+/−5 $cm^{-1}$, 2980+/−5 $cm^{-1}$, 2470+/−5 $cm^{-1}$, 1693+/−2 $cm^{-1}$, 1167+/−2 $cm^{-1}$, 1023+/−2 $cm^{-1}$ and 603+/−2 $cm^{-1}$. A KBr tablet is used when in determination, and the error range is determined according to the Chinese pharmacopoeia.

A thermal analysis result of the crystalline powder shows that the sample does not contain a crystalline solvent.

Another purpose of the invention is to disclose the preparation method of the Aildenafil citrate crystal form O, wherein, the Aildenafil citrate crystal form O can be obtained through the steps of: adding a mixture of distilled water and tetrahydrofuran which is 25 to 26 times of the amount of the Aildenafil citrate (weight-volume ratio, g/ml) into a reaction flask which is filled with the Aildenafil citrate, wherein the tetrahydrofuran takes 5% to 15% of the volume of the mixture; stirring, heating to reach the backflow temperature, filtering the mixture after 15 min to 20 min while heating, cooling the filtrate to be room temperature by stirring, insulating heat and stirring for 24 h to 26 h, precipitating and crystallizing, filtering, indoor placing for 1 h, and then moving to a vacuum drying oven to implement vacuum drying for 3 h.

The adopted Aildenafil citrate is prepared according to the following synthetic routes:

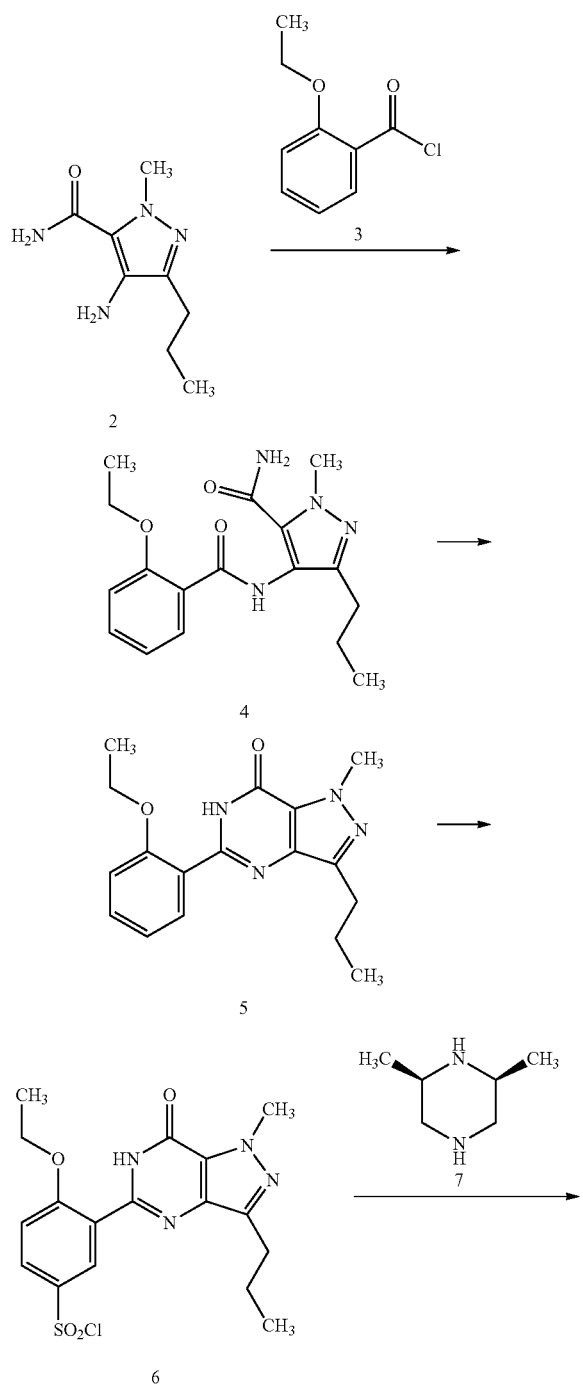

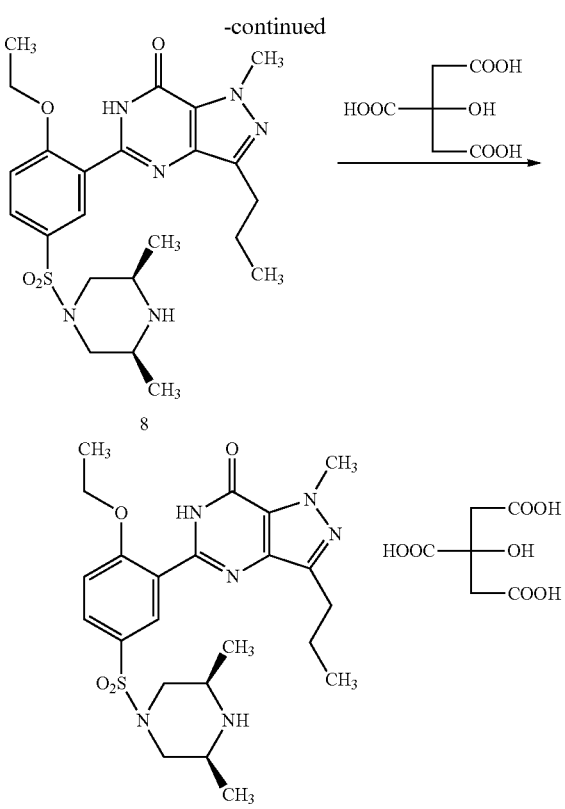

In the reaction formula:
Compound 2: 4-amino-1-methyl-3-n-propyl pyrazol-5-formamide
Compound 3: 2-ethoxybenzoyl chloride
Compound 4: 4-(2-ethoxybenzene amide)-1-methyl-3-n-propyl pyrazol-5-amide
Compound 5: 1-methyl-3-propyl-5-[(2-ethoxy) phenyl]-1,6-dihydro-7H-pyrazolo [4,3-d] pyridine-7-ketone
Compound 6: 1-methyl-3-propyl-5-[(2-ethoxy-5-sulfonyl) phenyl]-1,6-dihydro-7H-pyrazolo [4,3-d] pyridine-7-ketone
Compound 7: cis-2,6-dimethylpiperazine
Compound 8: Aildenafil
Compound 1: Aildenafil citrate Wherein, the compounds 2, 3, 7 can be purchased; however, if the compounds 2, 3, 7 cannot be purchased in market, they can be prepared from easily-obtained raw materials according to a conventional synthesis method based on the document precedents; for example, the compound 2 can be prepared according to the document (Chem. Pharm. Bull. 1984, 32(4):1568-1577; Fine Chemicals, 2001, 18(7):396-397, and the like); the compound 3 can be prepared according to the document (Chemical Research and Application, 2002, 14(5):605-607, and the like); and the compound 7 also can be conveniently prepared according to an existing document method.

Wherein, the compounds 4, 5, 6, 8 and the Aildenafil citrate can be prepared according to the method provided by the document (U.S. Pat. No. 4,666,908: Chinese Journal of Pharmaceuticals, 2000, 31(4):145-147; Chemical Research and Application, 2002, 14(5):605-607; Journal of Shenyang Pharmaceutical University, 2002, 19(3), 174-175, and the like); when using the compound 6 to prepare the compound 8, the Aildenafil (8) can be conveniently synthesized only by using the cis-2,6-dimethylpiperazine to replace the N-methyl piperazine. And the Aildenafil (8) can be recrystallized by methanol in order to obtain the Aildenafil citrate with higher purity. And then, the Aildenafil reacts with the equimolar citrate for 0.5 to 1 h under the backflow temperature in 23 to 28 times of methanol or ethanol (weight-volume ratio, g/ml), to generate the crude product of the Aildenafil citrate; the Aildenafil citrate is used for the researching the crystal form after being recrystallized by the methanol. Confirmed by the H Nuclear Magnetic Resonance ($^1$H-NMR), C Nuclear Magnetic Resonance ($^{13}$C-NMR) and the like, the chemical structure of the Aildenafil citrate is proved to be correct, as shown in FIG. 3 and FIG. 4.

The above reactions for preparing the Aildenafil citrate are conventional reactions, and those skilled in the art can know that, appropriate reagents and conditions of the conventional reactions can be easily determined with reference to ordinary textbooks and related documents.

Another purpose of the invention is to provide the pharmaceutical compositions which are prepared by combining the Aildenafil citrate crystal form O and the commonly-used pharmaceutical excipients, so as to prepare various oral preparations via the conventional methods.

Any known excipient which is widely applied in this field can be used in the pharmaceutical compositions, such as a carrier, a stuffing, an expansion agent, an adhesion agent, a humidizer, a disintegrating agent, a surfactant, a lubricant or a diluent. For example, the carrier includes, but is not limited by; lactose, refined sugar, sodium chloride, glucose, starch, calcium carbonate, crystalline cellulose and silicic acid. The adhesion agent includes, but is not limited by: water, ethanol, propyl alcohol, glucose solution, starch solution, gelatin solution, Carboxy Methylated Cellulose (CMC), methylcellulose, potassium phosphate and polyvinylpyrrolidone. The disintegrating agent includes, but is not limited by: dry starch, sodium alginate, agar powder, sodium bicarbonate, calcium carbonate, sodium dodecyl sulfate, glycerol monostearate, starch or lactose. The humidizer includes, but is not limited by: glycerin or starch. The lubricant includes, but is not limited by: purified talcum powder, stearate, boric acid powder and Polyethylene Glycol (PEG).

The preferred medicine delivery route of the pharmaceutical compositions provided by the invention is oral. The preparation formulation includes tablets, granules, capsules, sustained-release tablets, sustained-release micro-pellets and the like. And the tablets, granules and capsules are preferred.

The quantity of the Aildenafil citrate with this crystal form contained in the pharmaceutical composition takes 50 mg to 70 mg according to unit formulation.

The invention also provides the application of the Aildenafil citrate crystal form O in preparing the drugs for treating ED.

Pharmacodynamic study: determination for sexual function of castrated mice 60 Kunming strain mouse (feeding 60 mouse with 18 g to 22 g weight in the same period) are randomly divided into 6 groups, each 10 mouse per group, wherein, 5 groups of mouse are implemented with bilateral orchidectomy under ether anesthesia state to have castration treatment, and the rest one group of mouse are only implemented with surgical separation, without removing the testicles, which can be taken as a sham operation control group. Each group of mouse are fed in cage, and are tested after 3 d. The sham operation control group and the model control group are fed with 0.5% CMC, the castration group is fed with 2 mg·kg$^{-1}$, 6 mg·kg$^{-1}$ and 20 mg·kg$^{-1}$ of the Aildenafil citrate crystal form O, the positive control group is fed with 6 mg·kg$^{-1}$ of Sildenafil; all are ig delivery modes, and the dose volumes are all 10 ml·kg$^{-1}$. Putting the single male mice in the cage 60 min after feeding the drug, and adding one female mice in each cage, recording the time that the male mice firstly catches the female mice since the female mice is put in the cage (namely, the capture incubation period), and recording the back-climbing times of the male mice within 30 min. The results show that, 15 mg/kg$^{-1}$ can make the capture incubation period of the castrated mice be shortened by 201%, and make the capture times be increased by 4.4 times.

Influencing Factor Test:
Influence in Appearance

| Sample | Project | 0 month | 0.5 month | 1 month |
|---|---|---|---|---|
| Aildenafil citrate crystal form O | High-temperature test | White crystalline powder | White crystalline powder | White crystalline powder |
| | High-temperature test | White crystalline powder | White crystalline powder | White crystalline powder |
| | Illumination test | White crystalline powder | White crystalline powder | White crystalline powder |

Influence in Contents (High Performance Liquid Chromatography (HPLC) Area Normalization Method)

| Sample | Project | 0 month (%) | 0.5 month (%) | 1 month (%) |
|---|---|---|---|---|
| Aildenafil citrate crystal form O | High-temperature test | 99.96 | 99.96 | 99.95 |
| | High-temperature test | 99.96 | 99.95 | 99.96 |
| | Illumination test | 99.96 | 99.96 | 99.96 |

Influence in Related Articles

| Sample | Project | 0 month (%) | 0.5 month (%) | 1 month (%) |
|---|---|---|---|---|
| Aildenafil citrate compound crystal form O | High-temperature test | 0.04 | 0.04 | 0.04 |
| | High-temperature test | 0.04 | 0.04 | 0.05 |
| | Illumination test | 0.04 | 0.04 | 0.04 |

Influence in Infrared Absorption Spectrum

| Sample | Project | 0 month | 0.5 month | 1 month |
|---|---|---|---|---|
| Aildenafil citrate compound crystal form O | High-temperature test | As shown in FIG. 2 | Unchanged | Unchanged |
| | High-temperature test | As shown in FIG. 2 | Unchanged | Unchanged |
| | Illumination test | As shown in FIG. 2 | Unchanged | Unchanged |

Influence in PXRD

| Sample | Project | 0 month | 0.5 month | 1 month |
|---|---|---|---|---|
| Aildenafil citrate | High-temperature test | As shown in FIG. 1 | Unchanged | Unchanged |

-continued

| Sample | Project | 0 month | 0.5 month | 1 month |
|---|---|---|---|---|
| compound crystal form O | High-temperature test | As shown in FIG. 1 | Unchanged | Unchanged |
| | Illumination test | As shown in FIG. 1 | Unchanged | Unchanged |

The advantages of the invention are as follows:

From the above five tables, it can see that the appearance, PXRD and the infrared absorption spectrum of the Aildenafil citrate crystal form O are all unchanged in the case of high light (4500 lx+/−500 lx), high temperature (60+/−2° C.), high humidity (Relative Humidity (RH) 92.5%) from 0 to 1 month, and this shows that the crystal form is stable, without generating crystal transformation, and the original crystal form is still remained; additionally, as the related articles and the contents are unchanged, the crystal form O has excellent chemical stability, and is suitable for manufacturing and long-termly storing the drug preparations.

DETAILED DESCRIPTION OF THE EMBODIMENTS

In order to make those skilled in the art better understand the invention, the invention is further described with reference to the embodiments and drawings below. The embodiments are only used for explaining the invention, without limiting the range of the invention in any mode.

Figure 3:
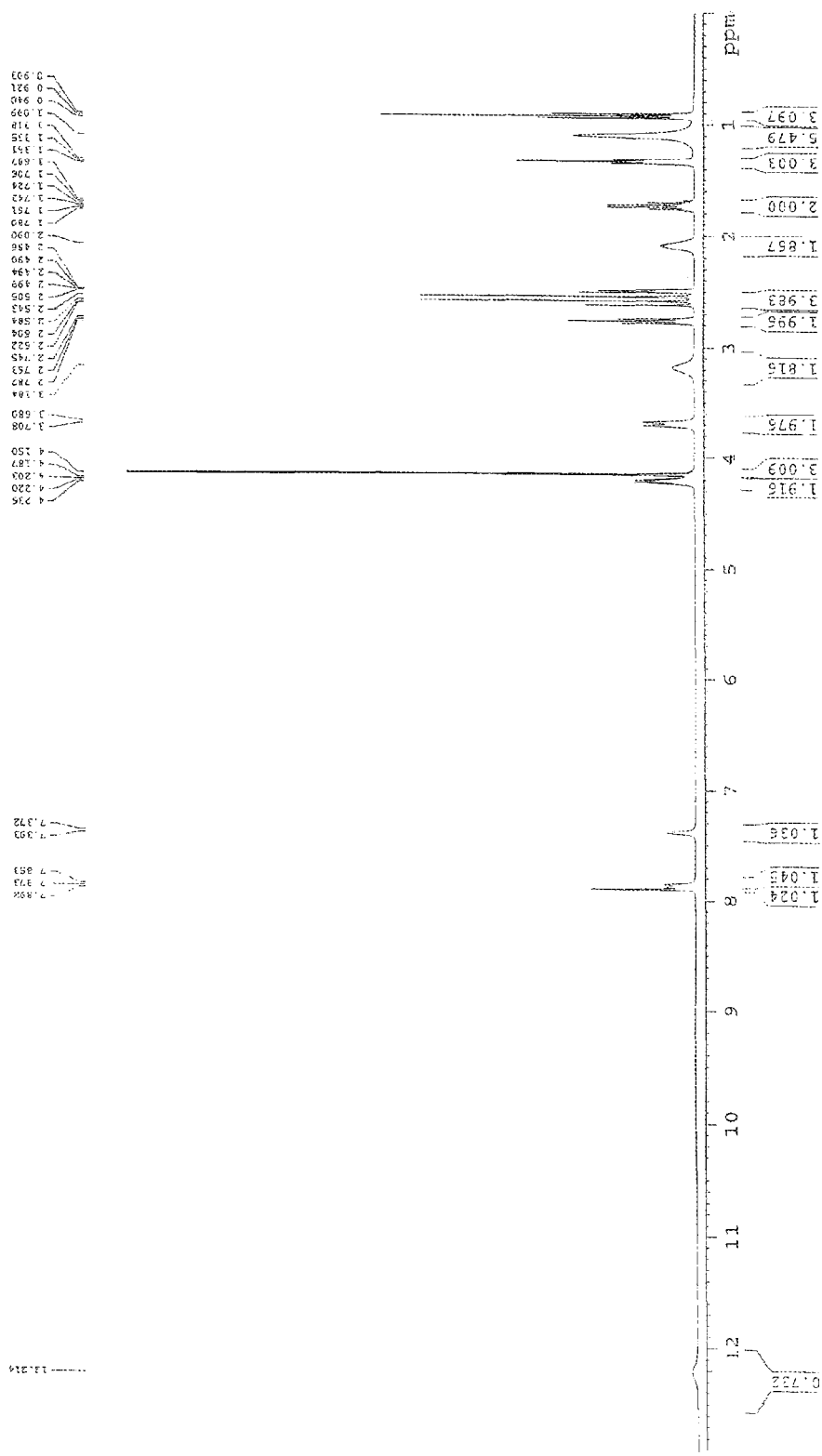
FIG. 3 shows the $^1$H-NMR of the Aildenafil citrate.
Figure 4:
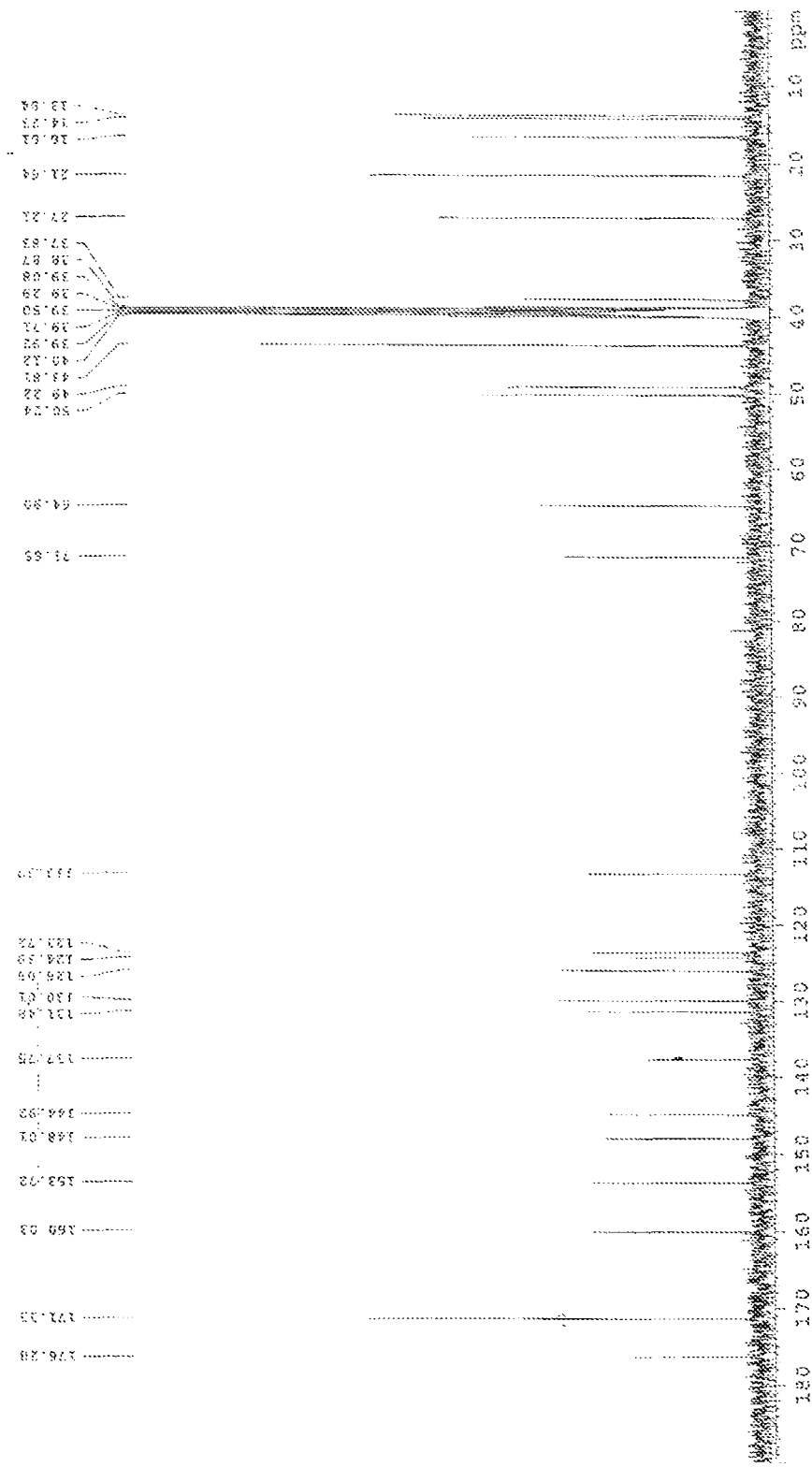
FIG. 4 shows the $^{13}$C-NMR of the Aildenafil citrate.

The Aildenafil citrate adopted in the invention has been descried before; and confirmed by elemental analysis, $^1$H-NMR, $^{13}$C-NMR, DEPT and High Resolution Mass Spectrometry (HRMS), the chemical structure of the Aildenafil citrate is correct, wherein, the $^1$H-NMR and the $^{13}$C-NMR are as shown in FIG. 3 and FIG. 4.

Embodiment 1

Figure 1:
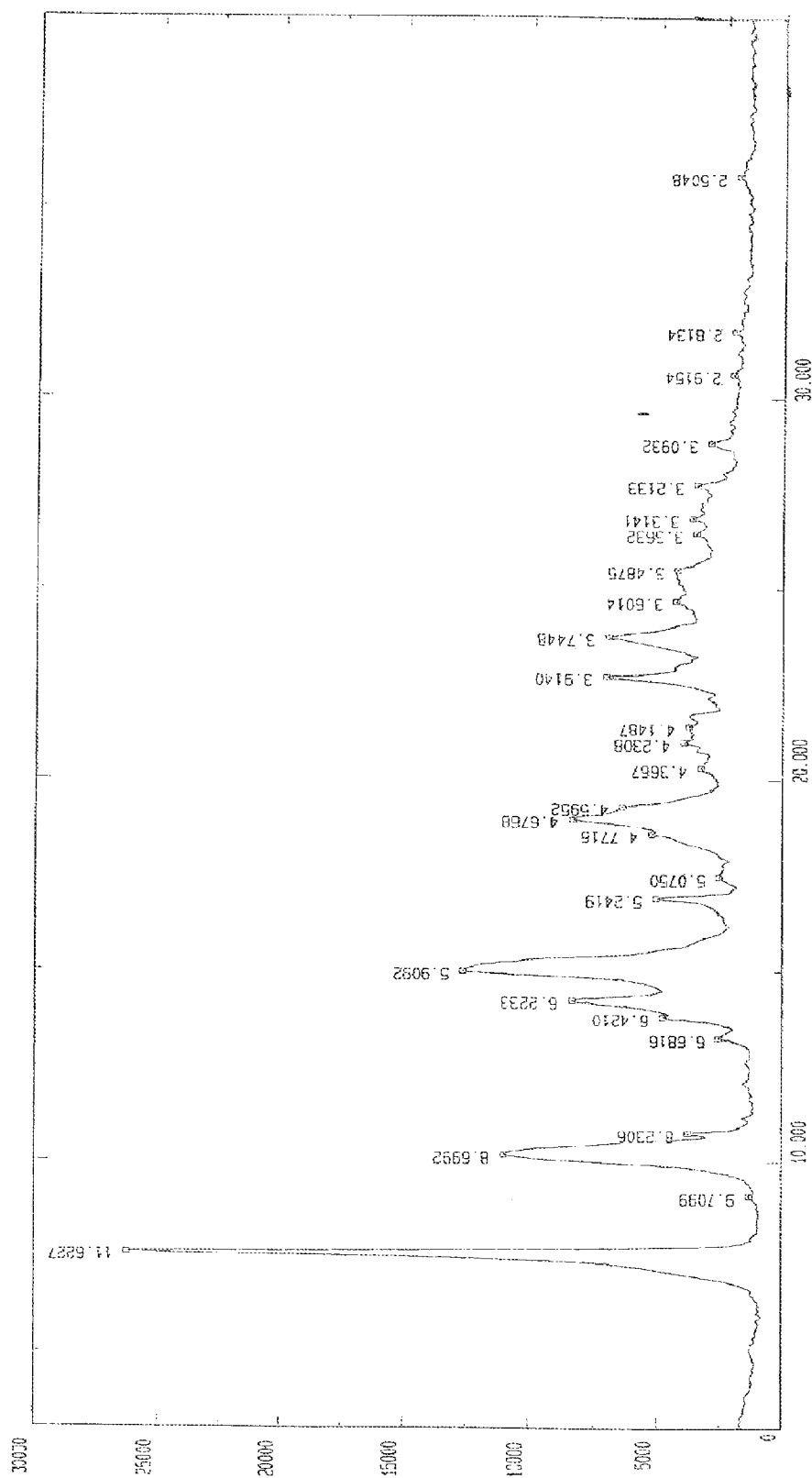
FIG. 1 shows a PXRD diagram of Aildenafil citrate crystal form O.
Figure 2:
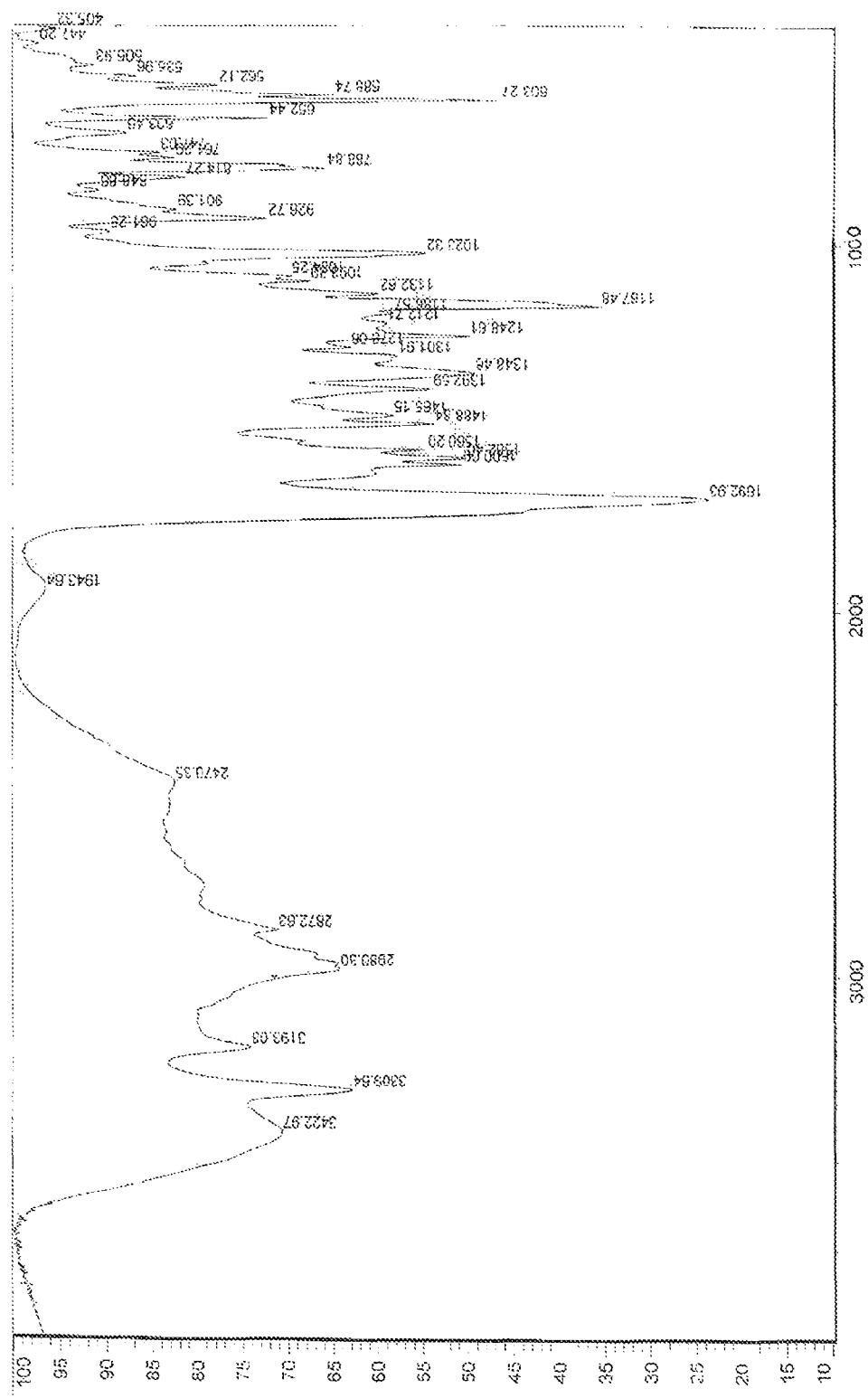
FIG. 2 shows an infrared spectrogram of the Aildenafil citrate crystal form O.

18.8 g Aildenafil citrate crystal form O can be obtained by adding 20 g Aildenafil citrate, 450 ml distilled water and 50 ml tetrahydrofuran in a 1000 ml reaction flask, stirring, heating to reach the backflow temperature, filtering while heating after 15 min, cooling the filtrate to reach the room temperature while stirring, insulating heat and stirring for 25 h, precipitating and crystallizing, filtering, indoor placing for 1 h, and then moving to a vacuum drying oven, vacuum drying for 3 h; the refining rate is 94%, the content is 99.96% via the determination of the HPLC area normalization method. The characteristics of the Aildenafil citrate crystal form O are displayed via the detection implemented by an X-ray diffraction instrument and an infrared spectrometer (as shown in FIG. 1 and FIG. 2).

Embodiment 2

37.6 g Aildenafil citrate crystal form O can be obtained by adding 40 g Aildenafil citrate, 900 ml distilled water and 95 ml tetrahydrofuran in a 2000 ml reaction flask, stirring, heating to reach the backflow temperature, filtering while heating after 20 min, cooling the filtrate to reach the room temperature while stirring, insulating heat and stirring for 25 h, precipitating and crystallizing, filtering, indoor placing for 1 h, and then moving to a vacuum drying oven, and vacuum drying for 4 h; the refining rate is 94%, the content is 99.96% via the determination of the HPLC area normalization method. The characteristics of the Aildenafil citrate crystal form O are displayed via the detection implemented by the X-ray diffraction instrument and the infrared spectrometer (as shown in FIG. 1 and FIG. 2).

Embodiment 3

Granules Containing the Aildenafil Citrate Crystal Form O

Prescriptions: using 50 g Aildenafil citrate crystal form O, 650 g lactose, 100 g crospovidone, 90 g PEG-4000, 135 g hydroxypropyl methyl cellulose and appropriate distilled water to preparing 1000 bags.

Technique: crushing the PEG-4000 together with the Aildenafil citrate crystal form O, screening through a 80-mesh sieve, uniformly mixing with other materials, and then using the distilled water to prepare flexible materials and to granulate, drying under low temperature to package as granules.

Embodiment 4

Capsules Containing the Aildenafil Citrate Crystal Form O

Prescriptions: using 60 g Aildenafil citrate crystal form O, 50 g starch, 40 g lactose, 10 g sucrose, 35 g microcrystalline cellulose, appropriate 10% polyvinylpyrrolidone ethanol solution and 1 g magnesium stearate to prepare 1000 capsules.

Technique: screening the Aildenafil citrate crystal form O and auxiliary materials via a 80-mesh sieve, weighing according to the prescription quantity, taking the 10% polyvinylpyrrolidone ethanol solution as the adhesion agent, and using a 16-mesh sieve to prepare proper granules, drying under 65° C., and granulating by using a 14-mesh sieve, adding the magnesium stearate to uniformly mix, measuring the granule content, calculating the filling quantity, and then filling into the capsules.

Embodiment 5

Tablets Containing the Aildenafil Citrate Crystal Form O

Prescriptions: using 70 g Aildenafil citrate crystal form O, 5 g microcrystalline cellulose, 140 g lactose, 10 g PEG-4000, 1 g magnesium stearate, 14 g polyvidone K30, 10 g croscarmellose sodium and appropriate distilled water to prepare 1000 tablets.

Technique: crushing the PEG-4000 together with the Aildenafil citrate crystal form O, screening through the 80-mesh sieve, using distilled water to prepare the flexible material after being uniformly mixed with other materials, using the 16-mesh sieve to granulate, drying in a drying box under 40° C. to 45° C., and adding the magnesium stearate into the dry granules to mix uniformly, and then tabletting.

The above is only the preferred embodiment of the invention; for those skilled in the art, changes can exist in the embodiments and the application range according to the ideas of the invention; thus, the contents of the description cannot be understood as the limitation of the invention.

INDUSTRIAL APPLICABILITY

The invention relates to a 1-[3-(6,7-dihydro-1-methyl-7-oxo-3-propyl-1H-pyrazolo[4,3-d] pyridine-5-group)-4-ethoxy-benzenesulfonyl]-cis-3,5-dimethylpiperazine citrate or Aildenafil citrate crystal form O and a preparation method thereof; and the invention also relates to the pharmaceutical compositions containing the Aildenafil citrate crystal form O and the use thereof in preparing drugs for treating ED; in this invention, the Aildenafil citrate crystal form O can be obtained by dissolving the raw material, namely, the Aildenafil citrate in a mixture of the distilled water and the tetrahydrofuran, stirring, heating, filtering, stirring filtrate, cooling, insulating heat, crystallizing, filtering and the like. The Aildenafil citrate crystal form O can be adopted to prepare the drugs with pharmaceutical excipients, and then used for so as to treat the male sexual dysfunction diseases. The Aildenafil citrate crystal form O provided by the invention can be produced in batch, and has excellent market prospects.

What is claimed is:

1. A method for preparation of an Aildenafil citrate crystal form O, exhibiting a powder X-ray diffraction (PXRD) determination, wherein a table diffraction angles 2θ with an error of +/−0.2, D values and relative intensities is provided as follows:

| Diffraction angle (2θ) | D value | Relative intensity (%) |
|---|---|---|
| 7.600 | 11.6227 | 100 |
| 10.160 | 8.6992 | 42 |
| 13.780 | 6.4210 | 18 |
| 14.220 | 6.2233 | 32 |
| 14.980 | 5.9092 | 48 |
| 16.900 | 5.2419 | 19 |
| 18.580 | 4.7716 | 20 |
| 18.960 | 4.6768 | 32 |
| 19.300 | 4.5952 | 24 |
| 20.980 | 4.2308 | 15 |
| 22.700 | 3.9140 | 27 |
| 23.740 | 3.7448 | 27 |
| 24.700 | 3.6014 | 16 |
| 25.520 | 3.4875 | 16 | the method comprising:
dissolving the Aildenafil citrate in 25 to 26 times (weight-volume ratio, g/ml) of a mixture of distilled water and tetrahydrofuran, wherein tetrahydrofuran takes 5% to 10% of a volume of the mixture;
stirring and heating to reach the reflux temperature;
filtering after 15 min to 20 min while heating, and cooling a filtrate to room temperature by stirring;
insulating heat and stirring for 24 h to 26 h, precipitating and crystallizing, filtering and drying.

2. The method according to claim 1, wherein, in an infrared spectrogram, values of the characteristic absorption peaks distinguishing the crystal form O from other crystal forms are 3423+/−5 cm$^{-1}$, 3310+/−5 cm$^{-1}$, 3193+/−5 cm$^{-1}$, 2980+/−5 cm$^{-1}$, and 2470+/−5 cm$^{-1}$.

3. The method according to claim 1, wherein, the Aildenafil citrate crystal form O does not contain a solvent.

4. The method according to claim 1, wherein, the Aildenafil citrate crystal form O is stable at least under conditions of 4500 lx+/−500 lx of light, 60+/−2° C., and/or relative humidity 92.5% for up to 1 month.

5. A pharmaceutical composition formed by admixture of the Aildenafil citrate crystal form O prepared according to claim 1 with one or more pharmaceutically acceptable carriers, excipients or diluents.

6. The pharmaceutical composition of the Aildenafil citrate crystal form O according to claim 5, wherein the carriers, excipients or diluents are oral preparations.

7. A method for treating Male Erectile Dysfunimction (ED) comprising: administering the pharmaceutical composition of claim 5 in an amount effective to treat Male Erectile Dysfunction (ED).

* * * * *